(12) United States Patent
Tyagi et al.

(10) Patent No.: US 7,662,550 B1
(45) Date of Patent: Feb. 16, 2010

(54) ASSAYS FOR SHORT SEQUENCE VARIANTS

(75) Inventors: Sanjay Tyagi, New York, NY (US);
Fred R. Kramer, Riverdale, NY (US);
David Alland, Chatham Township, NJ (US)

(73) Assignee: PHRI Properties, Inc., Newark, NJ (US)

( * ) Notice: Subject to any disclaimer, the term of this patent is extended or adjusted under 35 U.S.C. 154(b) by 416 days.

(21) Appl. No.: 10/110,907

(22) PCT Filed: Oct. 13, 2000

(86) PCT No.: PCT/US00/28515

§ 371 (c)(1),
(2), (4) Date: Jul. 24, 2002

(87) PCT Pub. No.: WO01/31062

PCT Pub. Date: May 3, 2001

(51) Int. Cl.
*C12Q 1/68* (2006.01)
*C12P 19/34* (2006.01)

(52) U.S. Cl. ............... 435/6; 435/91.2; 536/24.3; 536/25.32; 536/26.6

(58) Field of Classification Search ............ 435/6, 435/91.2; 536/24.3, 25.32, 26.6
See application file for complete search history.

(56) References Cited

U.S. PATENT DOCUMENTS

| 5,210,015 A | | 5/1993 | Gelfand et al. | |
|---|---|---|---|---|
| 5,328,825 A | * | 7/1994 | Warren et al. | 435/6 |
| 5,487,972 A | | 1/1996 | Gelfand et al. | |
| 5,925,517 A | | 7/1999 | Tyagi et al. | |
| 6,103,476 A | * | 8/2000 | Tyagi et al. | 435/6 |
| 6,461,817 B1 | * | 10/2002 | Alland et al. | 435/6 |

FOREIGN PATENT DOCUMENTS

WO    WO 99/40226    8/1999

OTHER PUBLICATIONS

Kostrikis et al., "Spectral Genotyping of Human Alleles", *Science*, vol. 279, pp. 1228-1229 (Feb. 20, 1998).
Piatek et al., "Molecular beacon sequence analysis for detecting drug resistance in *Mycobacterium tuberculosis*", Nature Biotechnology, vol. 16, pp. 359-363 (Apr. 1998).
Tyagi et al., "Molecular Beacons: Probes that Fluoresce upon Hybridization", Nature Biotechnology, vol. 14, No. 3, pp. 303-308 (Mar. 1996).
Marras et al., "Multiplex detection of single-nucleotide variations using molecular beacons", Genetic Analysis: Biomolecular Engineering, vol. 14, pp. 151-156 (1999).
Piatek et al., "Molecular beacon sequence analysis for detecting drug resistance in *Mycobacterium tuberculosis*", Nature Biotechnology, vol. 16, pp. 359-363 (Apr. 1998).
Vet et al., "Multiplex detection of four pathogenic retroviruses using molecular beacons", Proc. Natl. Acad. Sci. USA, vol. 96, pp. 6394-6399 (May 1999).
Tyagi, S. et al. "Multicolor molecular beacons for allele discrimination" Nature Biotechnology (1998) 16: 49-53.

* cited by examiner

*Primary Examiner*—Kenneth R. Horlick
*Assistant Examiner*—Joyce Tung
(74) *Attorney, Agent, or Firm*—Fox Rothschild LLP; Gerard P. Norton; Vyacheslav Vasilyev

(57) ABSTRACT

The invention provides assays that can detect multiple genetic variants of a gene (e.g., a mycobacterial gene) in a sample using a pool (e.g., 2, 3, 4, or more) of oligonucleotide hybridization probes.

17 Claims, 6 Drawing Sheets

ASSAYS FOR SHORT SEQUENCE VARIANTS

BACKGROUND OF THE INVENTION

Serious infections require early treatment with effective antibiotics [Mandell et al. (1995) Principles and practice of infectious diseases. 4th edition. Churchill Livingstone, N.Y.]. Because definitive identification of most bacteria, using a combination of culture, morphological and biochemical tests, usually requires several days to complete, most infectious diseases are treated empirically with broad spectrum antibiotics [Weinstein (1968) *Pediatr. Clin. North Am.* 15:141-156; Moellering (1974) *In: Seminar on Gram-Negative Infections.* St. Louis 1974:5; Cassiere et al. (1998) *Dis. Mon.* 44:613-675]. The emergence of multidrug-resistant bacteria has reduced the effectiveness of this practice. It has become increasingly difficult to find antibiotics (or combinations of antibiotics) that are reliably effective against all of the etiologic organisms of a specific syndrome. This problem is exacerbated where an unusual microbial (e.g., bacterial, mycoplasmal, viral, or parasitic) agent results in an infectious syndrome that can be confused with one caused by one (or more) more common pathogens. Simpler and more rapid identification methods and subsequent pathogen-specific therapy are becoming increasingly important in the treatment of infectious diseases [Casadevall (1996) *Clin Infect Dis.* 23:790-794]. U.S. Pat. Nos. 5,487,972, 5,538,848, and 5,925,517, published International Application No. WO 97/39008, and International Application No. PCT/US99/17145 are incorporated herein by reference in their entirety.

SUMMARY OF THE INVENTION

This invention provides a method for identifying the nucleotide sequence of a short region of DNA or RNA using multiple probes that hybridize to the region, wherein all or some of which are less than fully complementary to the region. This invention also provides a method to assess the relatedness of two nucleic acid regions when the sequence of one or both regions are unknown. Methods according to this invention have applications that include mutational analysis and pathogen identification.

Labeled oligonucleotide probes for use in methods of this invention are designed such that each will bind to multiple variants, or alleles, of a particular nucleic acid sequence. We refer to probes useful in methods of this invention as "sloppy" probes. When used in combinations, two or more such probes provide a means to detect the presence of one variant from among multiple possible variants. The invention provides an inexpensive and rapid diagnostic method that is able to identify a broad range of known and unknown microorganisms (e.g., bacteria, mycoplasmas, viruses, and parasites) and is easily automated. In addition, the assay can be used to identify genetic variants associated with mammalian (e.g., human) diseases such as cancer, autoimmune diseases, or metabolic diseases, or variations in genes of any eukaryotic organisms.

More specifically, the invention embodies a homogeneous detection assay for detecting, in a sample, a variant of a gene or any other short nucleotide sequence of up to about 50 nucleotides in length. The assay includes the steps of: (a) providing an aliquot of a sample suspected of containing a variant, the variant containing a first region; (b) forming a reaction mixture that includes the aliquot; (c) probing nucleic acid molecules in the reaction mixture with at least two (e.g., three, four, five, six, seven, eight, nine, ten, eleven, twelve, or fifteen) oligonucleotide hybridization probes having different target binding sequences hybridizable to the first region of the variant, the different probes being capable of generating in the reaction mixture separably detectable fluorescent signals indicative of their hybridization to the first region; (d) measuring the intensity of the signals; and (e) determining at least one ratio of fluorescence intensities emitted by the probes as an indication of the presence or absence of the variant in the sample.

The reaction mixture can be an amplification reaction mixture, with the assay further including, after forming the amplification reaction mixture, amplifying the first region, if present in the sample. The amplification reaction mixture can be a polymerase chain reaction (PCR) amplification mixture that includes a primer pair and an appropriate DNA polymerase. The primer binding regions are relatively conserved between the gene and the variant or among variants, as among bacterial species. Amplifications other than PCR that can be used in the assays of the invention include, without limitation, Q-Beta replicase-mediated amplification, transcription and replication reactions such as nucleic acid sequence-based amplification (NASBA) and self-sustained sequence replication (3SR), ligase chain reaction (LCR) or strand displacement amplifications (SDA).

The oligonucleotide hybridization probes, or sloppy probes, used in the assays of the invention are fluorescently labeled probes that produce a detectable signal in a homogeneous assay, that is, without having to separate probes hybridized to target from unbound probes. Suitable probes include dual-labeled probes having interactive labels consisting of a pair of fluorophores or a fluorophore and a quencher, such that hybridization to a target sequence or hybridization to a target sequence and reaction in the assay, e.g., cleavage by a polymerase in a PCR amplification, results in a detectable fluorescence signal. The probes can be added to the amplification reaction mixture before, during, or after the amplification. DNA polymerase used in an amplification, for example, a PCR amplification, can possess an exonucleolytic or endonucleolytic activity, and the oligonucleotide probes can be cleavable by the polymerase when the probes are hybridized to the first region. Examples of such probes are TaqMan™ probes [U.S. Pat. Nos. 5,487,972 and 5,538,848]. Alternatively, the probes can be pairs of linear probes that are complementary to one another and quench one another when they are hybridized to each other but not when hybridized to target [Morrison and Stols (1993) Biochemistry 32: 309-3104].

Most preferably, the sloppy probes are dual-labeled hairpin probes, described in U.S. Pat. No. 5,925,517, published International Application No. WO97/39008, and International Application No. PCT/US99/17145, all of which are incorporated herein by reference in their entireties. These hairpin probes contain a target binding sequence flanked by a pair of arms complementary to one another. They can be DNA, RNA, or PNA, or a combination of all three nucleic acids. Furthermore, they can contain modified nucleotides and modified internucleotide linkages. They can have a first fluorophore on one arm and a second fluorophore on the other arm, wherein the absorption spectrum of the second fluorophore substantially overlaps the emission spectrum of the first fluorophore. The probes need not be cleavable during amplification. Most preferably such hairpin probes are "molecular beacon probes" that have a fluorophore on one arm and a quencher on the other arm such that the probes are dark when free in solution. They can also be wavelength-shifting molecular beacon probes with, for example, multiple fluorophores on one arm that interact by fluorescence resonance energy transfer (FRET), and a quencher on the other arm. The target binding sequences can be, for example, 12 to 50, or 25 to 50 nucleotides in length, and the hybridizing arms can be 4 to 10 or 4 to 6 (e.g., 5 or 6) nucleotides in length. Molecular beacon probes can be tethered to primers, as described in Whitcombe et al. (1999), Nature Biotechnology 17:804-807.

Assays according to this invention can be chip-based, that is, utilizing sloppy probes immobilized at known locations on a solid surface. Conventional chip-based methods utilize immobilized probes that are specific for particular sequences. Replacing at least some of the conventional immobilized probes with sloppy molecular beacon probes and deriving sequence information from the pattern of hybridization to multiple probes as taught herein permits a reduction in the number of required immobilized probes by as much as an order of magnitude, in some assays by as much as two orders of magnitude.

The variants detected by the assays of the invention can contain a second region not overlapping the first region. If so, the assay can include the following additional steps: (f) probing nucleic acid molecules in the reaction mixture with a supplemental oligonucleotide hybridization probe having a target binding sequence hybridizable to the second region, if present, and not hybridizable to the first region, the supplemental probe being capable of generating in the assay reaction mixture a detectable signal indicative of its hybridization to the second region, wherein the signals emitted by each of the at least two probes and the supplemental probe are separably detectable; (g) measuring the intensity of the signal emitted by the supplemental probe; and (h) additionally determining at least one ratio of fluorescence intensities emitted by the supplemental probe and one of the at least two probes as part of the indication of the presence or absence of the variant in the sample. The supplemental probe is specific for the second region, that is, of conventional design.

The variants to be detected can be variants of eukaryotic genes, including mammalian genes. Thus the variant can be a somatic mutant of a mammalian gene, e.g., an oncogene (such as a ras mutation. Alternatively, it can be a mammalian allele or somatic mutant (e.g., an allele of the globin gene) associated with a metabolic disease (e.g., sickle cell anemia, thalassemia, cystic fibrosis, Gaucher disease) or an allele or somatic mutant (e.g., a major histocompatibility complex (MHC) gene, a immunoglobulin (Ig) gene, or a T cell receptor (TCR) gene) associated with an autoimmune disease (e.g., rheumatoid arthritis (RA), multiple sclerosis, insulin-dependent diabetes mellitus (IDDM), muscular dystrophy (MD), myasthenia gravis (MG), or systemic lupus erythematosus (SLE)).

Alternatively, the gene can be a microbial (e.g., bacterial, viral, or parasitic) allele. An example of an appropriate family of genes is the family of ribosomal RNA (rRNA) genes that contain highly conserved DNA sequences interspaced with variable species-specific regions [Woese (1987) *Microbiol. Rev.* 51:221-271]. DNA from a wide variety of microorganisms can be amplified using a single set of primers to conserved regions and species determination subsequently performed by analyzing species-specific sequences [Pace (1997) *Science,* 276:734-740]. A bacterial gene can be a *Mycobacterium* gene. Alleles of the mycobacterial 16S rRNA genes [Kirschner et al. (1993) *J. Clin. Microbiol.* 31:2882-2889; Vaneechoutte et al. (1993) *J. Clin. Microbiol.* 31:2061-2065; Kox et al. (1995) *J. Clin. Microbiol.* 33:3225-3233] can be used for mycobacterial species identification. In addition, rRNA alleles can be used to define species of *Gonococci* and *Chlamydia* [Kluytmans et al. (1991) *J. Clin. Microbiol.* 29:2685-2689; Iwen et al. (1995) *J. Clin. Microbiol.* 33:2587-2591]. Other conserved genes, such as rpoB or heat shock proteins, can also be used for bacterial species identification [Telenti et al. (1993) *Clin. Microbiol.* 31:175-178; Mollet et al. (1997) *Mol. Microbiol.* 26:1005-1011].

The invention also includes kits of reagents containing combinations of the above-mentioned probes for detecting any of the above mentioned genetic variants in a sample. Embodiments of kits may include chips having sloppy probes, preferably sloppy molecular beacon probes, immobilized at predetermined locations. The chips may also include supplemental probes or other conventional probes.

As used herein, "variants of a gene" are understood to include allelic variants and somatic mutants of a gene, and species-specific, subspecies-specific, and strain-specific versions of a gene. The "first region" of the variants, with which the "at least two oligonucleotide probes" employed in the assays of the invention hybridize, can differ from the equivalent region of the gene or other variations thereof by one or more nucleotide substitutions, one or more nucleotide additions, or one or more nucleotide deletions. While the at least two oligonucleotide hybridization probes can be capable of binding to the region of the gene equivalent to the first region of the variant, it is not required that they do so. It is understood that the term "variant" includes the complement of the relevant sequence.

As used herein, a "sample" can be one or more cells (eukaryotic or prokaryotic) a tissue, a cell or tissue lysate, a bodily fluid, excreta (e.g., urine or feces), a microbial colony or plaque, a solution containing nucleic acid (e.g., DNA, cDNA, or RNA) purified or semi-purified from any of the above sources, amplification (PCR or other) products either in the amplification reaction mixture or isolated from it.

As used herein, a "reaction mixture" is a solution in which probing with the at least two oligonucleotide hybridization probes (and optionally a supplemental oligonucleotide hybridization probe), as a step in the assay of the invention, is performed. The reaction mixture can be, for example, a solution composed of the "aliquot of the sample" only, or it can contain other components, e.g., buffer components. The reaction mixture can be an amplification (e.g., a PCR) reaction mixture and can contain the components necessary for an amplification reaction, e.g., nucleotides or deoxynucleotides, amplification primers or promoters, and enzymes (e.g., a DNA polymerase). If the assay includes amplification, the oligonucleotide hybridization probes can be added to the amplification reaction mixture before, during, or after amplification.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. In addition, the materials, methods, and examples are illustrative only and not intended to be limiting.

Other features and advantages of the invention, e.g., methods of identifying bacterial species in samples, will be apparent from the following description, from the drawings and from the claims.

DESCRIPTION OF THE PREFERRED EMBODIMENTS

The inventors have discovered that probes (sometimes referred to as "sloppy probes"), by virtue of their ability to bind to more than one (e.g., 2, 3, 4, 5, 6, 7, 8, 9, 10, 11, 12, 15, 20, 30, 40, 100, or 1000) variants of a given target sequence, can be used in assays to detect the presence of one variant of a nucleic acid sequence segment of interest from among a number of possible variants or even to detect the presence of two or more variants. The probes are used in combinations of two or more in the same assay. Because they differ in target binding sequence, their relative avidities for different variants are different. For example, a first probe may bind strongly to a wild-type sequence, moderately to a first allele, weakly to a second allele and not at all to a third allele; while a second probe may bind weakly to the wild-type sequence and the first variant, and moderately to the second variant and the third variant. Additional sloppy probes will exhibit yet different binding patterns due to their different target binding sequences. Thus, fluorescence emission spectra from combinations of sloppy probes define different microbial strains or species, as well as allelic variants of genes in mammalian tissues that are associated with diseases and somatic mutations.

Assays according to this invention are described below utilizing our most preferred sloppy probes, namely, "sloppy molecular beacon probes." Because sloppy probes reproducibly fluoresce with variable intensities after binding to different DNA sequences, combinations can be used in, for example, simple, rapid, and sensitive nucleic acid amplification reaction assays (e.g., PCR-based assays) that identify multiple pathogens in a single reaction well. It is understood, however, that the assays can be performed also on samples suspected of containing directly detectable amounts of unamplified target nucleic acids. This novel species identification assay is based on deconvolving the spectra of a set of partially hybridizing sloppy signaling probes, such as sloppy molecular beacon probes, each labeled with a fluorophore that emits light with a different wavelength optimum, to generate "signature spectra" of species-specific DNA sequences.

Operation Principles of Molecular Beacon Probes

Figure 1:
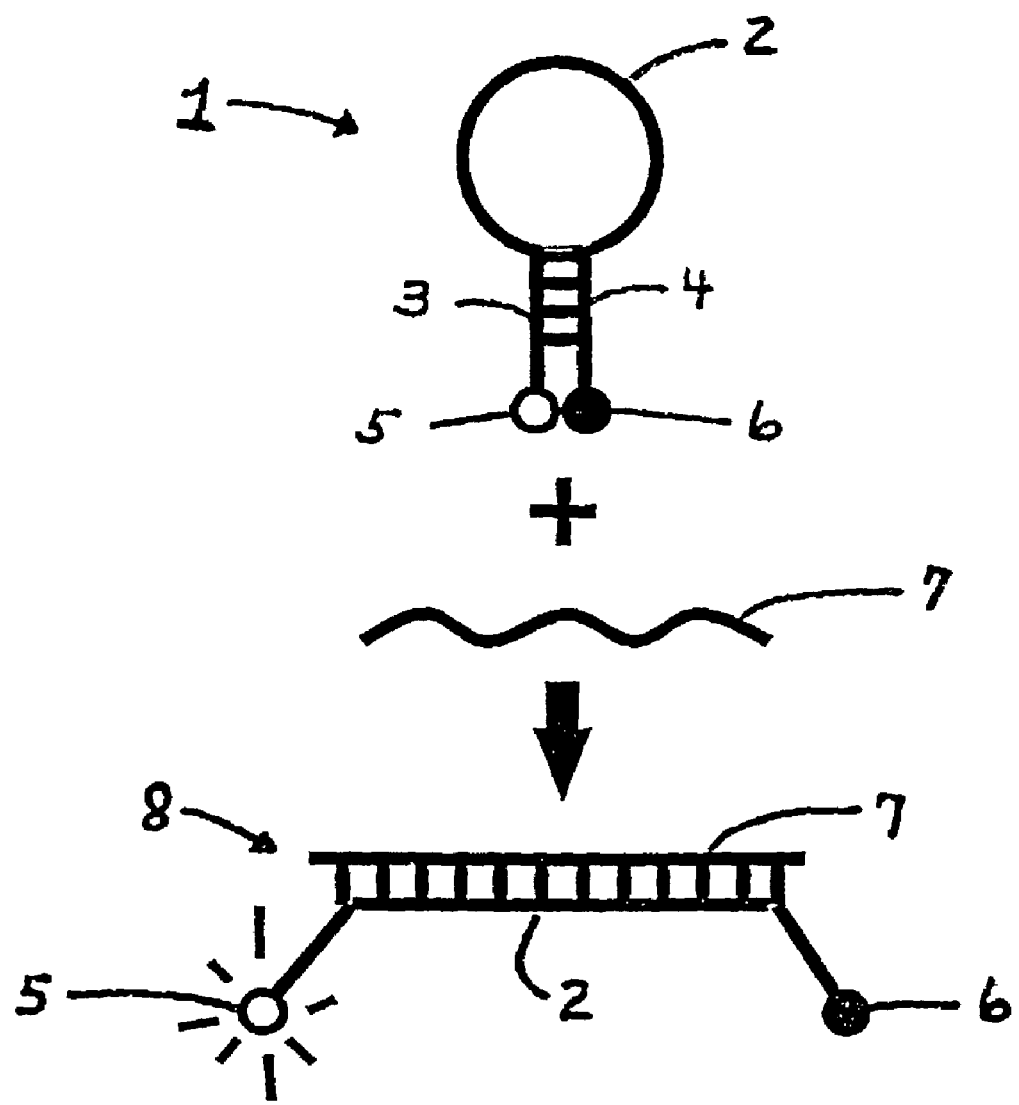
FIG. 1 is a depiction of the physical mechanism by which molecular beacons function as detection probes.

The use of conformation-dependent fluorescent probes called "molecular beacon" probes to detect short DNA sequences with single nucleotide accuracy in real-time PCR reactions has been described [Tyagi et al. (1996) *Nat. Biotechnol.* 14:303-308; Kostrikis et al. (1998) *Science,* 279: 1228-1229; Piatek et al. (1998) *Nat. Biotechnol.* 16:359-363]. With reference to FIG. 1 molecular beacon probe 1 is a single-stranded fluorescent nucleic acid molecule that possess a hairpin structure comprising loop 2 flanked by arms 3 and 4. Loop portion 2 serves as a probe sequence, or target binding sequence, that is complementary to a target DNA sequence. The probe sequence is embedded within short flanking arm sequences 3 and 4, which hybridize to each other to form a stem structure. In certain embodiments one arm sequence or a portion thereof may also be complementary to the target. A fluorescent moiety 5 is covalently linked to one arm, most conveniently at the free end, and a nonfluorescent quenching moiety 6 is covalently linked to the other arm, again, most conveniently at the free end. In homogenous solutions, the close proximity of the fluorophore to the quencher minimizes fluorescence, when the molecular beacon is in the stem-and-loop conformation. When the loop hybridizes to its target 7, the rigidity of the resulting probe-target helix 8 forces the arm sequences apart. The fluorophore 5 is thereby separated from the quencher 6, permitting the fluorophore to fluoresce brightly when excited by light of an appropriate wavelength.

Figure 2:
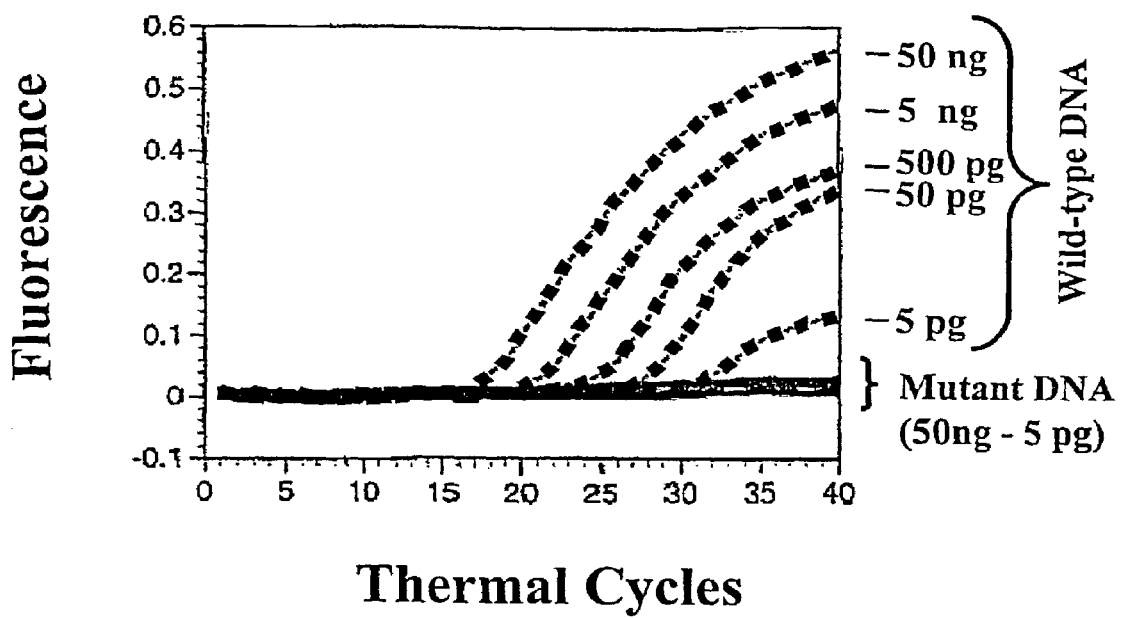
FIG. 2 is a line graph showing the increase in number, over time, of amplicons in a series of PCR amplifications as detected by molecular beacon probes.

Molecular beacon probes have a number of advantages for use in assays of this invention. Molecular beacons are able to detect amplicons as they are synthesized during amplification. In real-time PCR, for example, the fluorescence generated by molecular beacon-target hybrids can be measured, by a spectrofluorometric thermal cycler which plots the fluorescence intensity as a function of the number of PCR thermal cycles performed. FIG. 2 is a typical graph of a series of PCR reactions of an allele-discriminating molecular beacon probe, which may be used as the supplementary probe in methods of this invention, with varying starting amounts of perfectly matched target, wild-type DNA, and varying starting amounts of mutant DNA differing by a single nucleotide to which the probe essentially does not hybridize. The data in FIG. 2 indicate that, as increasing amounts of wild-type amplicon, but not mutant amplicon, are synthesized, the fluorescence due to the molecular beacon-target hybrids also increases, thereby resulting in a characteristic fluorescent curve. Reagents can be combined in, for example, the wells of a 96-well microtiter plate, or individual reaction tubes, which are then hermetically sealed. Molecular beacons with different target binding sequence can be labeled with differently colored fluorophores and used simultaneously in the same assay. Because the probes are dark when not hybridized, background fluorescence is low and separation of signals from multiple probes is improved. Amplification, molecular beacon hybridization, and analysis are all performed simultaneously.

Sloppy Molecular Beacons

Molecular beacon probes useful in the methods of this invention will hybridize to more than one variant and are herein designated "sloppy" molecular beacon probes. The probe sequences (i.e., the loop or the target hybridizing sequence) of sloppy molecular beacons are longer than the probe sequence of molecular beacon probes that hybridize only to perfectly matched target sequences. However, the sloppy molecular beacons used in the methods of the invention are not limited to a specific length of the target hybridizing sequence.

Persons skilled in the art can readily prepare sloppy probes by minimal trial and error. For random coil (or "linear") probes such as TaqMan™ probes described in U.S. Pat. No. 5,487,972, the length of the probe region complementary to intended targets is increased sufficiently that the probe binds not only to perfectly matched targets but also to targets differing, as need arises, by one or several nucleotides. For molecular beacon probes, the length of the probe region is increased but the length of the arms hybrid is kept short. We have found loop sequences in the range of 25 to 50 nucleotides in length and arms hybrids in the range of 4 to 6 nucleotides in length to be generally satisfactory and to provide an excellent starting point for probe design.

Figure 3A:
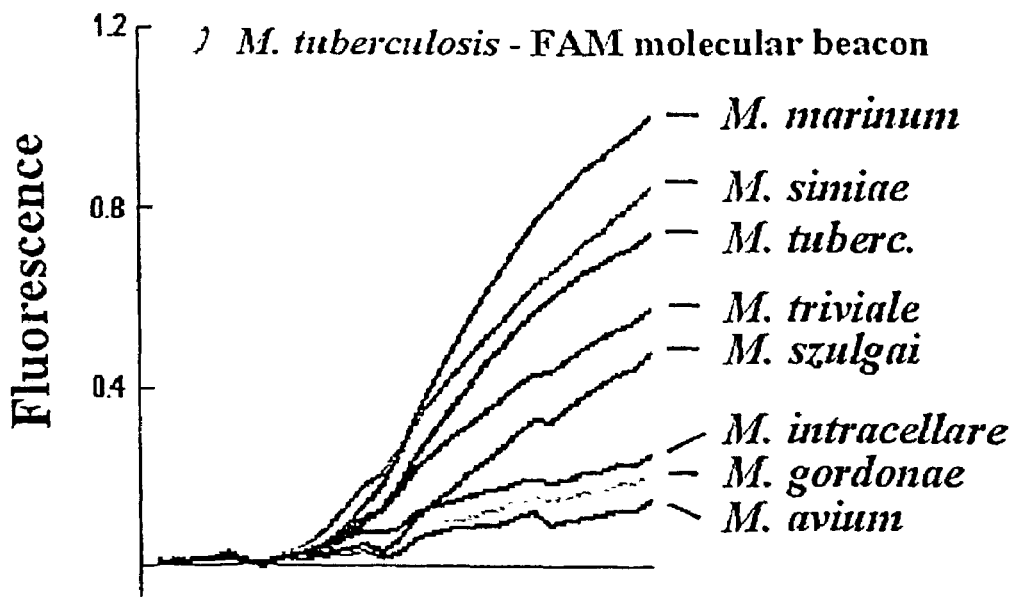
FIGS. 3A and 3B are line graphs showing the increase in number, over time, of amplicons in a series of PCR amplifications as detected by molecular beacon probes with target hybridizing sequences fully complementary to a target sequence in M. tuberculosis (FIG. 3A) and M. xenopie (FIG. 3B). Each line represents the data obtained from a PCR assay containing a template from a particular species of Mycobacteria.
Figure 3B:
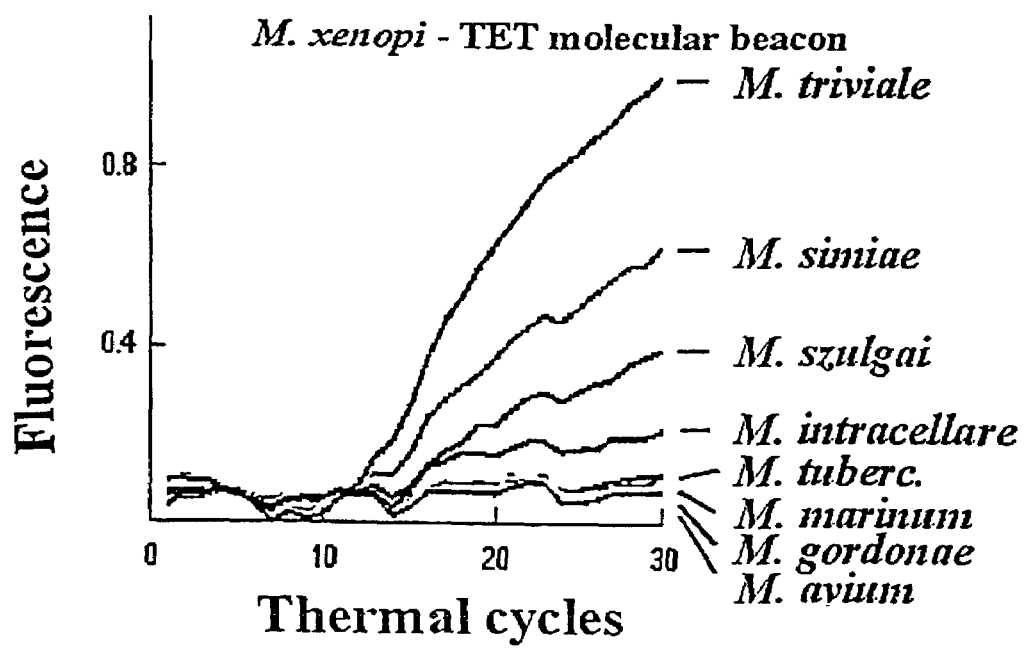

Sloppy molecular beacons can readily be designed to hybridize and fluoresce strongly to both perfectly complementary targets and to a wide range of mismatched targets at typical annealing temperatures, 40° C. to 55° C., of PCR assays. We performed real-time PCR assays containing sloppy molecular beacons using different target amplicons with varying degrees of complementarity to the probe region. FIGS. 3A and 3B show the results of real-time PCR assays using either a fluorescein (FAM)-labeled molecular beacon with a 45-nucleotide probe region that was perfectly complementary to a species-specific hypervariable region of the *M. tuberculosis* 16S rRNA gene (FIG. 3A) or a tetrachlorofluorescein (TET)-labeled molecular beacon with a 45-nucleotide probe region that was perfectly complementary to a species-specific hypervariable region of the *M. xenopie* 16S rRNA gene (FIG. 3B). As expected, these sloppy molecular beacons fluoresced strongly in the presence of perfectly complementary target during real-time PCR. However, they also demonstrated a wide range of fluorescence intensities when used in the presence of seven other partially non-complementary amplicons from other mycobacterial species. Gel electrophoresis demonstrated that the differences in fluorescence intensity were not due to differences in amplicon concentration, but rather, to the proportion of amplicons to which molecular beacons are bound at the annealing temperature of the assay. The target amplicons differed from *M. tuberculosis* or *M. xenopie* at 2-8 base pairs (4%-18% non-complementary with the probe region).

Every molecular beacon-target hybrid with a unique melting temperature will have a corresponding unique signal intensity at a defined temperature and concentration of probe and amplicon. Thus, a limited number of sloppy probes could be used as probes to identify many different possible target sequences in a real-time PCR reaction, if it were possible to control for differences in amplicon concentration, and to control for well-to-well variations in background fluorescence. Fluorescence intensity during real-time PCR is influenced by the concentrations of probes and amplicons present in the reaction. The concentration of probes can be controlled experimentally, but different amounts of amplicon are generated with each PCR reaction. In order to obtain measurements that are independent of target molecule concentration, assays according to this invention utilize the ratio of fluorescence of at least two differently colored sloppy probes, preferably molecular beacons. In calculating the ratios, the concentration parameters cancel out. As long as the same master mix of probes is used, the fluorescence ratio of two different sloppy molecular beacon probes hybridizing to the same target amplicon varied by less then 10% over a 10,000-fold change in target concentration.

Figure 4A:
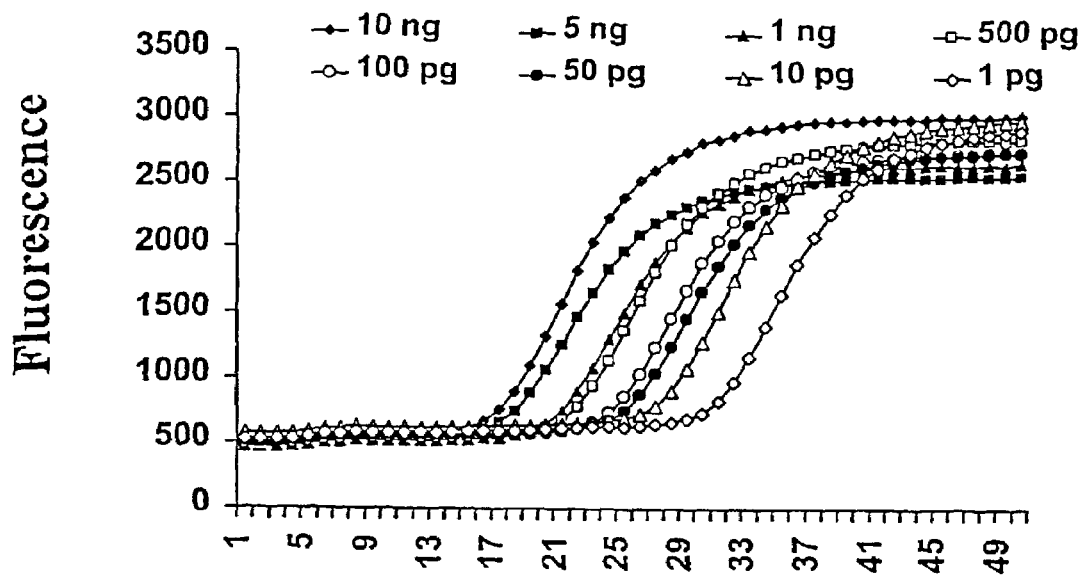
FIGS. 4A and 4B are line graphs showing the increase, over time, of fluorescence from a pair of molecular beacon probes in a series of PCR assays containing a range of concentrations of template.
Figure 4B:
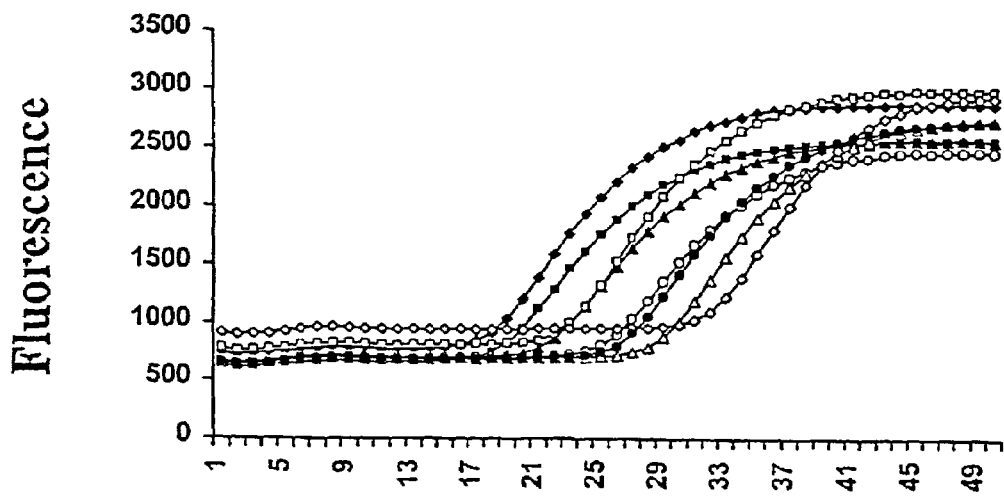
Figure 4C:
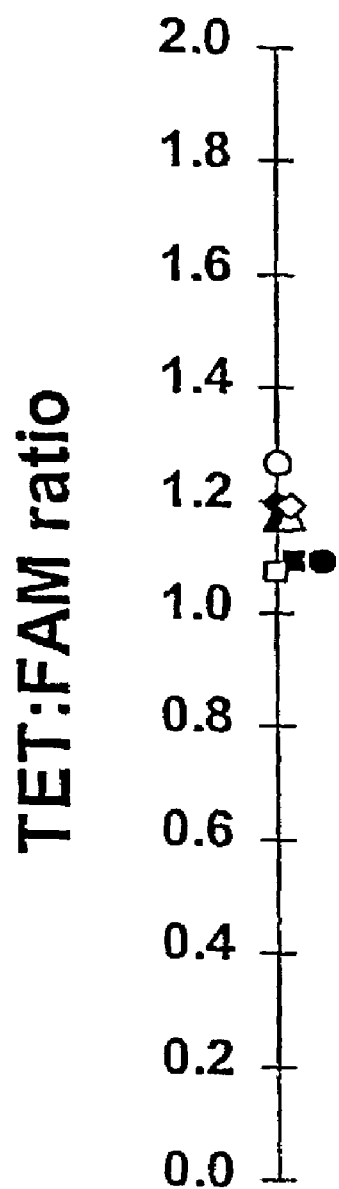
FIG. 4C presents the fluorescence ratios obtained from FIGS. 4A and 4B.

Referring to FIGS. 4A, 4B and 4C, a master mix containing two sloppy molecular beacon probes was prepared. One probe was labeled with TET. The other probe was labeled with FAM. The master mix was used in a series of PCR amplifications wherein eight amounts of starting concentration of target were used, varying from a maximum of 10 ng to a minimum of 1 pg. The TET-labeled probe was fully complementary to the target. The loop sequence of the FAM-labeled probe was fully complementary to a neighboring region of the target. FIG. 4A shows the fluorescence intensities obtained for the TET-labeled probe as a function of the number of PCR cycles performed. FIG. 4B shows the fluorescence intensities obtained for the FAM-labeled probe as a function of the number of PCR cycles performed. FIG. 4C is a plot of the ratios of TET intensities to FAM intensities. The non-variance of the ratios is apparent. In contrast, the fluorescence ratios of two sloppy molecular beacons hybridizing to two different target amplicons can vary by over 600%.

Mathematical models of molecular beacon-target interactions support these experimental observations. The inventors have determined mathematically that fluorescence has a linear relationship to target concentration, when the target concentration is sufficiently high. By analyzing fluorescence ratios (instead of individual fluorescence intensities), once the linear (or plateau) phase of PCR has been reached, the concentration dependence is canceled out (FIG. 4C). This enables a concentration independent measure of molecular beacon hybridization. Concentration effects are similarly eliminated in assays employing no amplification, with amplification other than PCR, and with other sloppy probes.

Sloppy Molecular Beacons Used in Combination to Identify Mycobacterial Species

An assay according to this invention generates fluorescence "fingerprints" of short DNA sequences that uniquely identify a particular DNA, even if the actual DNA sequence is not known. An example will be described utilizing four sloppy molecular beacon probes used to assay eight different mycobacterial species. Table 1 gives the sequences of a hypervariable species-specific region of the mycobacterial 16S rRNA gene for several species, showing nucleotides that differ from *M. tuberculosis* (M.tb).

TABLE 1

Species-specific DNA sequences within the hypervariable region A of selected mycobacterial 16S rRNA genes (SEQ ID NOs:1-19, respectively)

| | | | | | | | | | | | | | | |
|---|---|---|---|---|---|---|---|---|---|---|---|---|---|---|
| CGG | ATA | GG- | ACCA | CGG | GAT | TCA | TG | TCT- | TGT | GGT | GGA | AAG | CGC | *M. tb* complex |
| ... | ... | ...- | ...T | .AA | ..C | ... | .. | ...- | .C. | ... | ... | ... | .-- | *M. avium* |
| ... | ... | ...- | ...T | TAA | .GC | ... | .. | ...- | .TA | ... | ... | ... | .-- | *M. intracellulare* |
| ... | ... | ...- | ...T | TTA | ..C | ... | .. | ...- | .T. | ... | ... | ... | .-- | *M. intracellulare serovar* 18 |

TABLE 1-continued

Species-specific DNA sequences within the hypervariable region A of
selected mycobacterial 16S rRNA genes (SEQ ID NOs:1-19, respectively)

```
..A ... ..- ...T TTA ..C ... .. ...- .T. ... ... ... .-- M. intracellulare
                                                            serovar 7
... ... ..- ..TT .AA .GC ... .. ...- .T. ... ... ... .-T M. leprae
... ... ..- .... .TT .GC ... .. C..- ... ... ... ... .-- M. simiae
..A ... ..- ...T ..A .GC ... .. C..- ... ... ... ... .-- M. heidelbergense
... ... ..- ...T .TC .GC ... .. C..A G.A ... ... ... .-- M. intermedium
..A ... ..- ...C ..A .GC ... .. C..- ..G ... ... ... .-- M. malmoense
... ... ..- ...C ..A .GC ... .. C..- ..G ... ... ... .-- M. szulgai
... ... ..- ...T .AA .GC ... .. C..T ... ... ... ... .-- M. haemophilum
... ... T.- .... ... A.C ... .. .T.- ... ... ... ... .-- M. genavense
..A ... ..- .... .A. ..C A.. .. ..C- ... ... ... ... .-- M. gordonae I
..A ... ..- .... .A. A.C A.. .. ..C- ... ... ... ... .-- M. gordonae II
... ... ..- .... ... ... ... .. ..C- ... ... ... ... .-- M. asiaticum
... ... ..- .... ... ... T.. .. ..C- ... ... ... ... .-- M. marinum
... ... ..- .... .AT .TC ... .. GTG- ... ... ... ... .-- M. triviale
... ... ..- .... TTC TGC ... .. .GG- G.. ... ... ... .-- M. xenopi
```

We prepared four differently labeled sloppy molecular beacon probes, each of which had a target-hybridizing sequence (loop) that was complementary to one species. The sequences of the probes, including their 5-nucleotide arms, are shown in Table 2. The quencher in each case was DABCYL.

TABLE 2

Probe Sequences

M. AVIUM-TMR:

5' CGACG- CGG ATA GGA CCT CAA GAC GCA TGTCTT CTG
GTG GAA AGC T -CGTCG (SEQ ID NO:20)

M. XENOPI-TET:

5' CGACG- CGG ATA GGA CCA TTC TGC GCA TGT GGG GTG
GTG GAA AGC GT -CGTCG (SEQ ID NO:21)

M. tuberculosis.) -FAM:

5' CGATCGG- CGG ATA GGA CCA CGG GAT GCA TGT CTT GTG
GTG GAA AGC GCT -CCGATCG (SEQ ID NO:22)

M. FLAVESCENS-RhD:

5' CGACG- CGA ATA TTC CCT ATT GGT CGC ATGGCC TGG
TAG GGG AAA GCG CT -CGTCG (SEQ ID NO:23)

A master mix of the four sloppy probes was tested against eight different species. All six possible fluorescence ratios were determined, as described above in connection with FIG. 4C. A segment of 16S DNA from eight different mycobacterial species, each in a separate tube, was then amplified in the presence of all four sloppy molecular beacons. All of the PCR reactions used the same set of primers that hybridized to conserved sequences flanking the hypervariable sequence that identifies each species. Fluorescence was measured in real-time. In these experiments, the ABI 7700 spectrofluorometric thermal cycler derives an emission spectra for each fluorophore from the combined emissions of all four fluorophores in the reaction well. These data were then used to calculate fluorescence intensity for each sloppy molecular beacon. In order to normalize for differences in background fluorescence between each reaction well, the initial fluorescence in each well was subtracted from the final measured fluorescence at the end of the PCR reaction in the same well.

Figure 5:
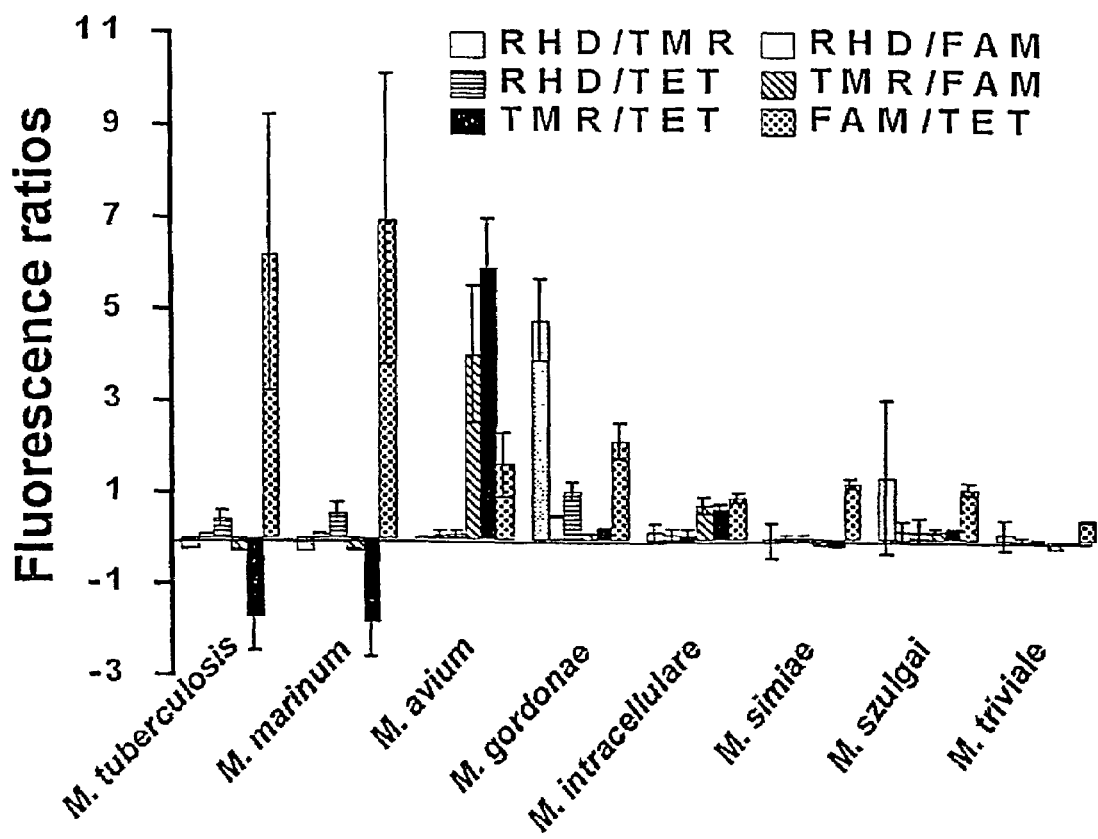
FIG. 5 is a bar graph showing the ratios of fluorescence intensity calculated for eight PCR assays containing template DNA from one of eight different species of Mycobacterium and four different sloppy molecular beacon probes.

A ratio of fluorescence values between each two molecular beacons present in the tube was generated, resulting in six fluorescence ratios per tube. A unique set of fluorescence ratios (fluorescence fingerprints) was thus derived for the 16S DNA sequence for each species tested (FIG. 5). The experiments were then repeated three times. FIG. 5 shows the mean ratio from the three repeats. It also includes error bars showing the data spread from the mean. The negativity of some ratios is an artifact of the ABI fluorescence calculations and does not imply the disappearance of fluorescence. The negative values can be used accurately to calculate fluorescence ratios.

Each DNA sequence generated a characteristic fluorescence fingerprint. Importantly, the diversity of fluorescence ratios relates to the degree of sequence diversity among the target amplicons. The ratios were most similar for M. tuberculosis and M. marinum, whose sequences in the target region only differ from one another at two nucleotide positions (Table 1). The ratios obtained for less closely related species differed markedly. Subsequent experiments confirmed the accuracy of this pattern. Despite the similarity of M. tuberculosis and M. marinum, none of the triplicate RHD/FAM ratios overlapped between these two species, demonstrating that the ratios were unique to each species. For M. tubercu-

*losis*, the RHD/FAM ratios were −0.23+/−0.01, while for *M. marinum* the RHD/FAM ratios were −0.29+/−0.005. All of the other species also had at least one fluorescence ratio where none of the triplicate measurements overlapped with the ratio of any other species.

A potential problem in the assays of the invention arises when more than one allele or allelic amplicon is present in the same reaction well, making deconvolution of spectra very difficult. Examples of such situations include: (a) analyses of samples (e.g., tissue, blood, excretions, or secretions) that contain more than one species, subspecies, or strain of a particular pathogenic micro-organism (e.g., mycobacteria); and (b) analysis of DNA from eukaryotic cells that are heterozygous for the variant sequence of interest. Where mammalian tissues, blood, or other bodily fluids are being tested, the chance of infection by related bacterial species is low; hence, only one variant of a gene is likely to occur in a sample. Where bacterial gene variants are encountered in a sample, this problem can be obviated by using DNA from individual colonies as a source of template.

An alternative solution to the problem is to perform the PCR amplifications in multiple vessels (e.g., wells of a microtiter plate) in each of which there is less than one genome-equivalent of the DNA. If there is a single variant present in the original sample, in vessels giving a positive result (i.e., showing significant fluorescence ratios), there should be monophasic distribution of values, i.e., all the vessels should yield a similar value within the precision of the method. If there are two variants in the sample, there should be a biphasic distribution of values among the positive PCR reaction vessels. In one set of vessels, the ratios will cluster around a first value indicative of one variant (e.g., a wild-type allele) and in the second set vessels, around a second value indicative of a second variant (e.g., a mutant allele). Where three variants are present, a triphasic distribution would be obtained, and so on. The content of reaction vessels giving anomalous values which do not fall into a particular group can be isolated and the amplicons sequenced to test for the presence of two or more amplicons in the wells.

The use of multiple (e.g., 3, 4, 5, 6, 8 or 10) sloppy beacon probes and calculation of all possible ratios can overcome discrimination problems due, for example, to the ratio of fluorescence intensity ratio for a single sloppy molecular beacon pair being the same for two or more candidate target sequences.

Wavelength-shifting Molecular Beacons

Four different sloppy molecular beacons may in some cases be insufficient to resolve a large number and variety of target sequences with high precision. The number of different sloppy molecular beacons that can be used simultaneously in the same assay well is only limited by the ability to resolve the emission spectrum of each fluorophore. One of the factors that limits the sensitivity of detection by fluorescence is that the optimal emission wavelength of most fluorophores is only a few nanometers longer than their optimal excitation wavelength (Stokes shift). As a consequence of this, a portion of the excitation light reaches the detector by processes such as scattering and reflection, contributing to a background signal that limits the sensitivity. Monochromatic light sources, such as lasers, are often used to minimize the extent to which the excitation light reaches the detector. However, this prevents the use of a large number of different fluorophores in the same solution, because these light sources excite some fluorophores very well but excite other fluorophores not as well or not at all. For example, the commonly used blue argon ion laser is suitable for exciting fluorescein but not Texas red, because it excites Texas red only at about two percent of its optimal level.

Wavelength-shifting molecular beacons (International Application No. PCT/US99/17145, incorporated herein by reference in its entirety) permit more different probes to be used with a monochromatic light source. A wavelength-shifting molecular beacon probe can be excited, for example, by a blue argon ion laser, but emit strong fluorescent light in the orange, red, or near-infrared wavelengths. Wavelength-shifting molecular beacons contain a harvester fluorophore and an emitter fluorophore on one arm, plus a quencher such as DABCYL on the other arm. The harvester, the emitter, and quencher can be disposed in a number of positions with respect to each other. The harvester fluorophore is chosen to have high absorbance in the wavelength range of the available monochromatic light source. The emitter fluorophore is chosen to have high absorbance in the wavelength range of the harvester's emission. Whereas the blue argon ion laser will not excite Texas red, fluorescein will. Thus, a wavelength-shifting molecular beacon with a fluorescein harvester and Texas red emitter is excited quite well by the same light source. In a hairpin conformation when not bound to target, the quencher quenches fluorescence, and wavelength-shifting molecular beacons emit little light in the emission ranges of either fluorophore. The light energy absorbed by the harvester fluorophore is efficiently channeled to the quencher moiety and is lost as heat. When the probe sequence in the loop binds to its target and the arms are forced apart and the quencher is no longer effective. In this conformation, the harvester and emitter fluorophore interact. The fluorescence of the harvester fluorophore is not restored, because its stored energy is rapidly transferred via resonance energy transfer (FRET) to the emitter fluorophore that is placed at an appropriate (FRET) distance. The emitter fluorophore then emits the received energy in its own characteristic range of emission thereby providing a large Stokes shift.

Although the invention has been described with reference to the preferred embodiment, it should be understood that various modifications can be made without departing from the spirit of the invention. Accordingly, the invention is limited only by the following claims.

What is claimed is:

1. A homogeneous detection assay method for identifying which variant among multiple variants of a short nucleotide sequence is present in a sample, said multiple variants differing from one another by one or more changes selected from the group of nucleotide substitutions, deletions and additions, comprising:

(a) providing a reaction mixture containing the sample with at least three hybridization probes having different target binding sequences, said probes being capable of hybridizing to mismatched targets in the assay, and said probes being differently fluorescently labeled probes whose hybridization can be detected without separating unbound probes, wherein each of said probes is capable of hybridizing to more than one variant of said multiple variants with varying degrees of complementarity;

(b) measuring the intensity of fluorescence signals resulting from hybridization of each of said probes; and (c) identifying which variant is present by determining a fluorescence fingerprint for the sample, said fluorescence fingerprint comprising ratios of the intensities of the fluorescence signals of the at least three probes.

2. The method of claim 1, wherein said reaction mixture is an amplification reaction mixture, the method further comprising, after forming said amplification reaction mixture containing said probes, amplifying said short nucleotide sequence.

3. The method of claim 2, wherein said amplification reaction mixture is a PCR amplification mixture that includes a primer pair and a DNA polymerase.

4. The method of claim 3, wherein said DNA polymerase possesses exonucleolytic or endonucleolytic activity and wherein said hybridization probes are cleavable during said PCR amplification by said polymerase when hybridized to said short nucleotide sequence.

5. The method of claim 3, wherein each of the last three probes has a single-stranded loop target-binding sequence of 25-50 nucleotides in length and an arms hybrid.

6. The method of claim 5, wherein said probes are constructed from modified nucleotides.

7. The method of claim 1, wherein each of said probes has a single-stranded loop target-binding sequence of 25-50 nucleotides in length and an arms hybrid.

8. The method of claim 7, wherein said short nucleotide sequence has a length of up to about fifty nucleotides.

9. The method of claim 7, wherein said short nucleotide sequence is a gene sequence.

10. The method of claim 7, wherein said probes are immobilized at preselected locations on a solid surface.

11. The method of claim 7, wherein said short nucleotide sequence is a mammalian gene.

12. The method of claim 7, wherein said short nucleotide sequence is a microbial gene.

13. The method of claim 12, wherein said microbial gene is a bacterial gene.

14. The method of claim 13, wherein said bacterial gene is a mycobacterial gene.

15. The method of claim 11, wherein said gene is an oncogene.

16. The method of claim 11, wherein said gene is associated with a metabolic disease.

17. The method of claim 11, wherein said gene is associated with an autoimmune disease.

* * * * *

SEQUENCE LISTING

<160> NUMBER OF SEQ ID NOS: 23

<210> SEQ ID NO 1
<211> LENGTH: 41
<212> TYPE: DNA
<213> ORGANISM: Mycobacterium tuberculosis -continued

```
<400> SEQUENCE: 1
cggataggac cacgggattc atgtcttgtg gtggaaagcg c                          41

<210> SEQ ID NO 2
<211> LENGTH: 41
<212> TYPE: DNA
<213> ORGANISM: Mycobacterium avium

<400> SEQUENCE: 2
cggataggac ctcaagactc atgtcttctg gtggaaagcg c                          41

<210> SEQ ID NO 3
<211> LENGTH: 41
<212> TYPE: DNA
<213> ORGANISM: Mycobacterium intracellulare

<400> SEQUENCE: 3
cggataggac ctttaggctc atgtctttag gtggaaagcg c                          41

<210> SEQ ID NO 4
<211> LENGTH: 41
<212> TYPE: DNA
<213> ORGANISM: Mycobacterium intracellulare serovar 18

<400> SEQUENCE: 4
cggataggac ctttagactc atgtcttttg gtggaaagcg c                          41

<210> SEQ ID NO 5
<211> LENGTH: 41
<212> TYPE: DNA
<213> ORGANISM: Mycobacterium intracellulare serovar 7

<400> SEQUENCE: 5
cgaataggac ctttagactc atgtcttttg gtggaaagcg c                          41

<210> SEQ ID NO 6
<211> LENGTH: 41
<212> TYPE: DNA
<213> ORGANISM: Mycobacterium leprae

<400> SEQUENCE: 6
cggataggac ttcaaggctc atgtcttttg gtggaaagcg t                          41

<210> SEQ ID NO 7
<211> LENGTH: 41
<212> TYPE: DNA
<213> ORGANISM: Mycobacterium simiae

<400> SEQUENCE: 7
cggataggac cacttggctc atgccttgtg gtggaaagcg c                          41

<210> SEQ ID NO 8
<211> LENGTH: 41
<212> TYPE: DNA
<213> ORGANISM: Mycobacterium heidelbergense

<400> SEQUENCE: 8
cgaataggac ctcgaggctc atgccttgtg gtggaaagcg c                          41

<210> SEQ ID NO 9
<211> LENGTH: 42
<212> TYPE: DNA
```

-continued

<213> ORGANISM: Mycobacterium intermedium

<400> SEQUENCE: 9
cggataggac ctctcggctc atgcctagga ggtggaaagc gc    42

<210> SEQ ID NO 10
<211> LENGTH: 41
<212> TYPE: DNA
<213> ORGANISM: Mycobacterium malmoense

<400> SEQUENCE: 10
cgaataggac cccgaggctc atgccttggg gtggaaagcg c    41

<210> SEQ ID NO 11
<211> LENGTH: 41
<212> TYPE: DNA
<213> ORGANISM: Mycobacterium szulgai

<400> SEQUENCE: 11
cggataggac cccgaggctc atgccttggg gtggaaagcg c    41

<210> SEQ ID NO 12
<211> LENGTH: 42
<212> TYPE: DNA
<213> ORGANISM: Mycobacterium haemophilum

<400> SEQUENCE: 12
cggataggac ctcaaggctc atgcctttgt ggtggaaagc gc    42

<210> SEQ ID NO 13
<211> LENGTH: 41
<212> TYPE: DNA
<213> ORGANISM: Mycobacterium genavense

<400> SEQUENCE: 13
cggatatgac cacggaactc atgttttgtg gtggaaagcg c    41

<210> SEQ ID NO 14
<211> LENGTH: 41
<212> TYPE: DNA
<213> ORGANISM: Mycobacterium gordonae I

<400> SEQUENCE: 14
cgaataggac cacaggacac atgtcctgtg gtggaaagcg c    41

<210> SEQ ID NO 15
<211> LENGTH: 41
<212> TYPE: DNA
<213> ORGANISM: Mycobacterium gordonae II

<400> SEQUENCE: 15
cgaataggac cacagaacac atgtcctgtg gtggaaagcg c    41

<210> SEQ ID NO 16
<211> LENGTH: 41
<212> TYPE: DNA
<213> ORGANISM: Mycobacterium asiaticum

<400> SEQUENCE: 16
cggataggac cacgggattc atgtcctgtg gtggaaagcg c    41

<210> SEQ ID NO 17
<211> LENGTH: 41

-continued

```
<212> TYPE: DNA
<213> ORGANISM: Mycobacterium marinum

<400> SEQUENCE: 17
cggataggac cacgggattc atgtcctgtg gtggaaagcg c                41

<210> SEQ ID NO 18
<211> LENGTH: 41
<212> TYPE: DNA
<213> ORGANISM: Mycobacterium triviale

<400> SEQUENCE: 18
cggataggac cacatgtctc atggtgtgtg gtggaaagcg c                41

<210> SEQ ID NO 19
<211> LENGTH: 41
<212> TYPE: DNA
<213> ORGANISM: Mycobacterium xenopi

<400> SEQUENCE: 19
cggataggac cattctgctc atgtggggtg gtggaaagcg c                41

<210> SEQ ID NO 20
<211> LENGTH: 50
<212> TYPE: DNA
<213> ORGANISM: Mycobacterium avium

<400> SEQUENCE: 20
cgacgcggat aggacctcaa gacgcatgtc ttctggtgga aagctcgtcg       50

<210> SEQ ID NO 21
<211> LENGTH: 51
<212> TYPE: DNA
<213> ORGANISM: Mycobacterium xenopi

<400> SEQUENCE: 21
cgacgcggat aggaccattc tgcgcatgtg gggtggtgga aagcgtcgtc g     51

<210> SEQ ID NO 22
<211> LENGTH: 56
<212> TYPE: DNA
<213> ORGANISM: Mycobacterium tuberculosis

<400> SEQUENCE: 22
cgatcggcgg ataggaccac gggatgcatg tcttgtggtg gaaagcgctc cgatcg  56

<210> SEQ ID NO 23
<211> LENGTH: 54
<212> TYPE: DNA
<213> ORGANISM: Mycobacterium flavescens

<400> SEQUENCE: 23
cgacgcgaat attccctatt ggtcgcatgg cctggtaggg gaaagcgctc gtcg   54
```